United States Patent [19]

Sugaya et al.

[11] Patent Number: 5,081,038
[45] Date of Patent: Jan. 14, 1992

[54] ANALYTICAL METHOD AND APPARATUS USING CHEMICAL ANALYTICAL SLIDES

[75] Inventors: Fumio Sugaya; Hirotoshi Endo, both of Saitama, Japan

[73] Assignee: Fuji Photo Film Co., Ltd., Kanagawa, Japan

[21] Appl. No.: 586,324

[22] Filed: Sep. 19, 1990

Related U.S. Application Data

[63] Continuation of Ser. No. 167,654, Mar. 14, 1988, abandoned.

[30] Foreign Application Priority Data

Mar. 12, 1987 [JP] Japan .................. 62-055255

[51] Int. Cl.⁵ .................................................. G01N 35/00
[52] U.S. Cl. .................................. 436/46; 436/63; 436/527; 422/57; 422/63; 422/64; 422/72
[58] Field of Search ............... 422/297, 57, 63, 64, 422/72; 436/527, 63, 808, 46

[56] References Cited

U.S. PATENT DOCUMENTS

| | | | |
|---|---|---|---|
| 3,907,503 | 9/1975 | Betts et al. | 2/ |
| 4,152,390 | 5/1979 | Nosco et al. | 422/57 |
| 4,224,032 | 9/1980 | Glover et al. | 436/46 |
| 4,234,538 | 11/1980 | Ginsberg et al. | 422/64 |
| 4,234,539 | 11/1880 | Ginsberg et al. | 422/67 |
| 4,430,299 | 2/1984 | Horne | 422/64 |
| 4,512,952 | 4/1985 | Blanding et al. | 436/46 |
| 4,517,160 | 5/1985 | Galle et al. | 422/65 |
| 4,647,431 | 3/1987 | Sekine et al. | 436/46 |
| 4,764,342 | 8/1988 | Kelln et al. | 422/63 |

FOREIGN PATENT DOCUMENTS

| 156835 | 9/1983 | Japan | 422/64 |
|---|---|---|---|
| 078362 | 7/1984 | Japan | 422/64 |

OTHER PUBLICATIONS

Discroll et al., Discrete Automated Chemistry System with Tableted Reagents, Clin. Chem., vol. 29, No. 9, 1983, 1609-1615.
Rubin et al., Automation of Patient/Sample Linkage. Identification and Analysis, Clin. Chem. 21/7,1975, p. 977.
American Dade, Stratus System Brochure, #CH-16-15-2/7-82, distributed by American Scientific Products, 1982.

Primary Examiner—Robert J. Warden
Assistant Examiner—Lyle A. Alexander
Attorney, Agent, or Firm—Sughrue, Mion, Zinn Macpeak & Seas

[57] ABSTRACT

An analytical method using chemical analytical slides which includes the steps of: placing liquid samples in an automatic sampler of an analyzer, loading in to said analyzer the chemical analytical slides combined in groups according to respective analytes to be measured in each sample, including a partition plate interposed between said groups of the chemical analytical slides, and changing over the sample to be spotted on the chemical analytical slide by means of said automatic sampler when said partition plate is detected.

By employing this method, the sample to be spotted can be precisely and synchronously changed, and therefore, serious error is prevented that might occur if the analytical result of a different person is used to distinguish between analytes. Moreover, the analytical operation is simple and highly efficient.

15 Claims, 4 Drawing Sheets

ANALYTICAL METHOD AND APPARATUS USING CHEMICAL ANALYTICAL SLIDES

This is a continuation of application Ser. No. 07/167,654 filed Mar. 14, 1988 now abandoned.

BACKGROUND OF THE INVENTION

1. Field of the Invention

This invention relates to an analytical method using chemical analytical slides used for the determination of various components in a body fluid such as blood or urine.

2. Description of the Prior Art

Recently, in the clinical assay field, the advantages of dry analysis in simplicity and rapidity have been appreciated, and this method has widely been utilized. In the dry analysis, a liquid sample such as blood is spotted on a chemical analytical slide containing the reagents reacting with the object component such as glucose or urea nitrogen of the sample to produce color change such as coloring or discoloring, and the content of the object component is colorimetrically determined.

The dry analysis is usually carried out by using an automatic analyzer in order to secure accurate measurement and simplicity. In the analyzer, usually chemical analytical slides are arranged in a cartridge, and the cartridge is loaded in the cartridge loading part. The loaded chemical analytical slides are intermittently delivered one by one to the spotting part, and a liquid sample is spotted on each chemical analytical slide by a pipette. The slide is then transferred to an incubator, and warmed therein to proceed coloring reaction. Then, the color produced in each chemical analytical slide is optically measured at the photometric part to determine respective analytical subjects.

Meanwhile, there are various chemical analytical slides such as for determining glucose, urea nitrogen, hemoglobin and uric acid. Since several components of a sample are analyzed usually at once, various chemical analytical slides are combined for each sample according to its analytical items, and stacked in a prescribed order. For example, when glucose and urea nitrogen in sample I and glucose, urea nitrogen and total protein in sample II were measured, respective chemical analytical slides were arranged in the cartridge in the order of chemical analytical slide for glucose, the slide for urea nitrogen, the slide for glucose, the slide for urea nitrogen and the slide for total protein from the bottom. The changing of the sample was carried out by the worker handling the sample when the worker judged the new group of incoming slides by visual observation.

In such a method, however, the changing of the samples was often done in error to resulting in a serious problem that the analytical result of a different person was used for diagnosis of disease and the like. Moreover, since the worker had to judge respective chemical analytical slides one by one by visual observation before spotting the next sample, the system was complicated and its efficiency was low.

SUMMARY OF THE INVENTION

An object of the invention is to provide a method for analysis of liquid samples using chemical analytical slides for detecting various components in the liquid samples, capable of correctly changing the liquid samples.

Another object of the invention is to provide an analytical method using chemical analytical slides of which analytical operation is simple and highly efficient.

The above objects of the present invention have been achieved by interposing a partition plate between the chemical analytical slide groups for respective samples, and changing over the samples to be spotted by an automatic liquid sampler based upon the detection of this partition plate.

Thus, the analytical method using chemical analytical slides of the invention comprises: placing liquid samples in an automatic sampler of an analyzer, loading the chemical analytical slides combined in the group according to respective analytes to be determined of each sample, together with a partition plate interposed between said group and another group of the chemical analytical slides in the analyzer, and changing over the sample to be spotted on the chemical analytical slide by means of said automatic liquid sampler when said partition plate is detected.

DETAILED DESCRIPTION OF THE INVENTION

Figure 2:
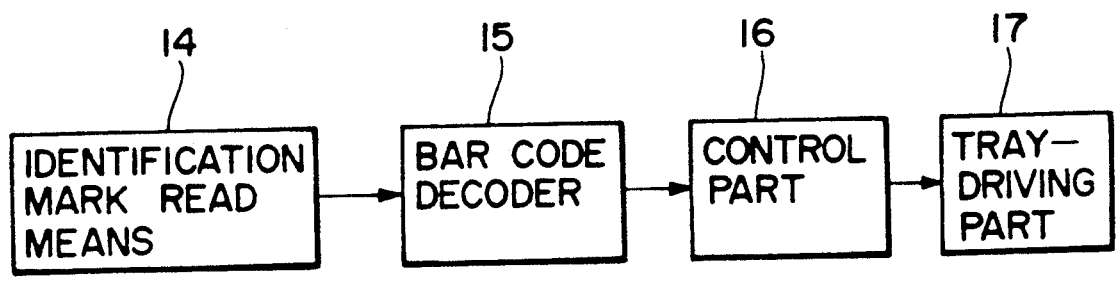
FIG. 2 is a block diagram of tray-driving circuit.

The partition plate may be made of paper such as cardboard or carton, plastic, metal, wooden board, glass or the like. The partition plate may have a size and a thickness capable of delivery into the analyzer using chemical analytical slides. For smooth delivery, it has preferably a similar figure to the chemical analytical slide and the same size as or slightly smaller than the slide. The partition plate should be discriminable optically from the chemical analytical slide. For example, an identification mark such as a bar code different from the bar code of the chemical analytical slide is provided on the surface of the partition plate, and each partition plate is detected by reading the bar code optically. The bar code of the partition plate may be one kind, and it is used only for changing over the sample to be spotted. While, each bar code may be different, and the sample is identified by the partition plate. Besides, square code such as shown in FIG. 2 of Japanese Patent KOKAI 59-125162 may also be utilized. As the changing over means of samples, either of a sampling pipette or the sample placed on a rotary tray may be moved. Moreover, the receiver of sample may also be provided with an identification mark same as that of the partition plate. In this arrangement, and when the partition plate having an identification mark is detected, the receiver having the same identification mark is selected for spotting.

Examples of the sample suitable for the analytical method of the invention are whole blood, blood plasma, blood serum, urine, cerebrospinal fluid and the like, and the components to be measured include glucose, urea nitrogen, hemoglobin, ammonia, uric acid, total bilirubin, total protein, total cholesterol, calcium and the like.

EXAMPLES

Figure 1:
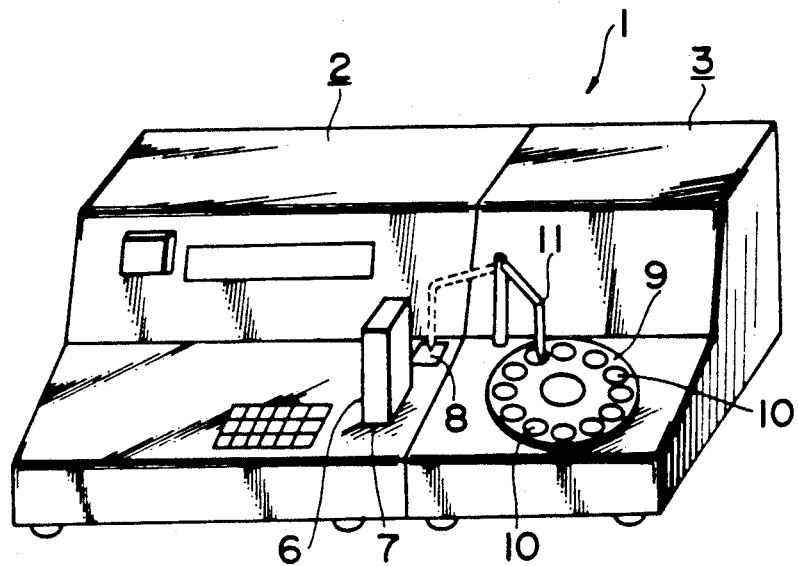
FIG. 1 is a perspective view of a chemical analytical apparatus used for conducting the analytical method of the invention using chemical analytical slides.
Figure 8:
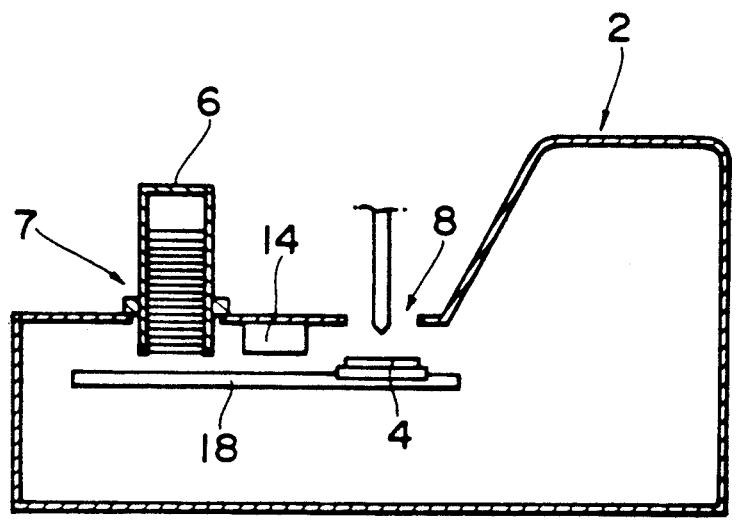
FIG. 8 is a sectional view of the chemical analytical apparatus.

The chemical analytical apparatus 1 used for conducting the method of the invention is composed of an analyzer 2 and an automatic sampler 3, as shown in FIG. 1. The analyzer 2 is provided with a cartridge loading part 7 loaded with the cartridge 6 containing chemical analytical slides 4 and partition plates 5 arranged in a prescribed order and a spotting station 8 to spot a sample on the chemical analytical slide delivered from the cartridge loading part 7. As shown in FIG. 8, a photoelectric read means 14 to read the bar code of the chemical analytical slide and the identification mark of the partition plate is provided in the passage from the cartridge loading part 7 to the spotting station 8. 18 denotes slide delivery means. The analyzer 2 is also provided with an incubator (not illustrated) for incubating the chemical analytical slide and a photometric part (not illustrated) for measuring the coloration in the chemical analytical slide in its inside.

Figure 4:
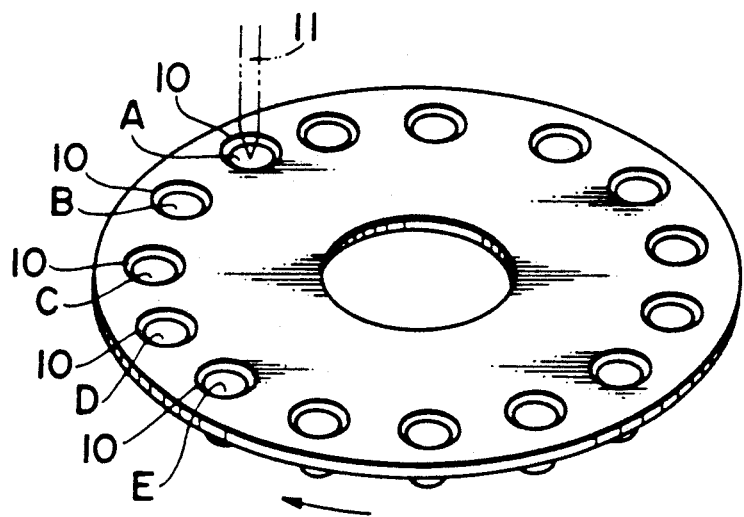
FIG. 4 is an enlarged perspective view of the tray part of the automatic sampler illustrated in FIG. 1.

A circular tray 9 is rotatably provided on the front upper face of the automatic sampler 3. The tray 9 is provided with circular holes at a regular intervals in its circumferential direction near the margin, and each cup 10 for receiving sample is hung by engaging the flange of the cup with the edge of the hole, as shown in FIG. 4. The automatic sampler is also provided with a pipette 11 for spotting sample near the tray 9. The pipette 11 capable of rotating reciprocally between the cup 10 and the spotting part 8.

The photoelectric read means 14 is, as shown in FIG. 2, connected to a tray-driving part 17 through a bar code decoder 15 and a control part 16. The identification mark of the partition plate is detected by the photoelectric read means 14. The signal from the read means 14 is judged by the bar code decoder, and the result is inputted into the control part 16. The signal from the bar code decoder 15 is recognized by the control part 16, and in the case of the partition plate, it orders the tray-driving part 17 to drive and the tray 9 is forced to rotate the angle necessary to replace the cup 10 with the next one.

By using the above chemical analytical apparatus, the following components of various samples are measured as follows:

| Sample | Cup | Measuring Item (Analyte) |
| --- | --- | --- |
| A | A | Glucose (GLU). |
|   |   | Urea Nitrogen (BUN) |
| B | B | GLU, BUN, Total Protein (TP) |
| C | C | GLU, Total Bilirubin (TBIL), Ammonia (NH₃), TP |
| D | D | Hemoglobin (HB), Uric Acid (UA), Total Cholesterol (TCHO) |
| E | E | Calcium (CA), GLU, BUN |

Figure 3:
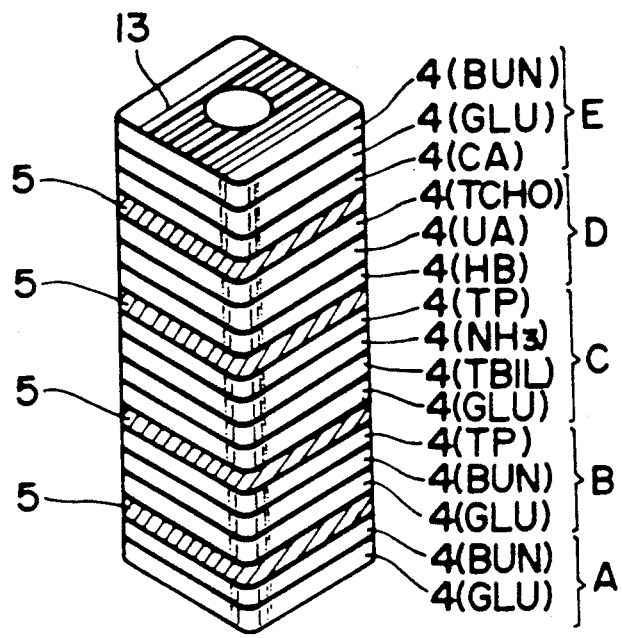
FIG. 3 is a perspective view indicating the stacked state of chemical analytical slides used for the method of the invention.

Chemical analytical slides above are loaded in the cartridge according to the measuring order of the samples. That is, as shown in FIG. 3, the chemical analytical slide for glucose (4 (GLU)) and the chemical analytical slide for urea nitrogen (4 (BUN)) being the measuring items of Sample A are stacked in the cartridge, and then a partition plate 5 is further stacked thereon. The chemical analytical slide groups (4 (GLU), 4 (BUN), 4 (TP)) of Sample B are stacked on the above partition plate 5 successively, and a partition plate 5 is stacked on it. The stackings of the chemical analytical slides 4 and partition plate 5 are repeated to complete the arrangement shown in FIG. 3.

Figure 5:
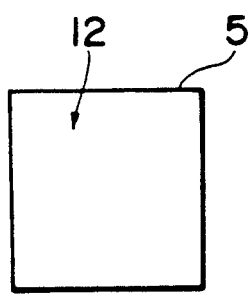
FIGS. 5 to 7 are plan views of various partition plates used in the method of the invention.

As shown in FIG. 3, a bar code 13, different according to the measuring item, is printed on each chemical analytical slide 4. While, the surface of the partition plate 5 is, as shown in FIG. 5, made white and printed with no opaque bar, this being the identification mark 12.

On the other hand, as shown in FIG. 4, each sample is put into a cup 10, and respective cups are set in the holes of the tray 9 in the prescribed order.

After the chemical analytical slide is set in the above mentioned state, the chemical analytical apparatus is started. The first chemical analytical slide 4 (GLU) of Sample A is delivered to the spotting station 8, where a prescribed amount of Sample A is spotted on it by the pipette 11. On the passage from the cartridge loading part 7 to the spotting station 8, the bar code 13 printed on the chemical slide is detected by means of the read means 14. This chemical analytical slide is transferred to the incubator, and warmed therein to proceed coloring reaction. Then, the color produced is measured at the photometric part. After the second chemical analytical slide 4 (BUN) is treated similarly, the partition plate 5 is delivered to the spotting station 8. At this time, since the surface of the partition plate 5 passing under the read means 14 is white without opaque bar, the signal outputted from the read means 14 is judged as the signal indicating the partition plate 5 by means of the bar code decoder 15. The result is outputted from the bar code decoder 15 to the control part 16, and the control part 16 orders the tray-driving part 17 to drive and forces the tray 9 to rotate the angle to change the cup 10 with the new cup 10 for receiving Sample B. Then, the delivery of the chemical analytical slide 4 and spotting are repeated. When the next partition plate 5 comes, the tray 9 rotates again and the next cup 10 for receiving Sample C comes just under the pipette 11 at the spotting station 8. These actions are repeated, and the measurements of all items of all samples finish.

Figure 6:
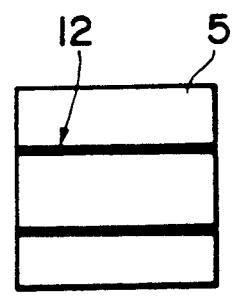

Another example of partition plate 5 is illustrated in FIG. 6. The identification mark 12 composed of relatively thick two bars is printed on the partition plate 5.

Figure 7:
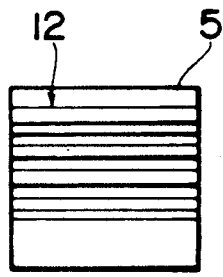

Another example of partition plate 5 is illustrated in FIG. 7. The bar code of same kind as that used for chemical analytical slide is printed on the partition plate 5 as the identification mark 12, and the same bar code 12 is also printed on a cup 10 set on the tray 9 as shown in FIG. 4. The read means 14 reads the bar code of this partition plate 5, and the cup 10 having the same bar code is located just under the pipette 11 by the order of the control part 16. In this example, the order of the cups 10 set on the tray 9 is not necessary to consistent with the order of the chemical analytical slides 4 stacked in the cartridge 6.

We claim:

1. A method of automatically dispensing samples onto chemical analytical slides in an automatic analytical analyzer comprising the steps of:

placing liquid samples in an automatic sampler of an analyzer;

arranging chemical analytical slides by groups according to respective analyzes to be measured for each of said samples;

interposing a partition plate which is optically discriminable from said chemical analytical slides between adjacent ones of said groups of said chemical analytical slides;

loading said chemical analytical slides and said partition plate in said analyzer;

automatically moving said groups of said chemical analytical slides and said partition plate along a path through a dispensing station to a chemical analyzer;

dispensing a first one of said samples onto a first one of said groups of chemical analytical slides at said dispensing station;

detecting the presence of said partition plate between said groups of said chemical analytical slides in said path; and in response to the detection of said partition plate, immediately dispensing a second one of said samples onto a next adjacent group of chemical analytical slides at said dispensing station.

2. The analytical method of claim 1, further comprising the step of moving said samples relative to said dispensing station; and wherein said loading step comprises vertically stacking said groups of chemical analytical slides and said partition plate in said analyzer; and wherein each dispensing step comprises drawing a sample into a pipette and dispensing the samples from said pipette onto said groups of slides at said dispensing station.

3. The analytical method of claim 1, wherein said loading step comprises stacking said groups of chemical analytical slides and said partition plate in said analyzer.

4. The analytical method of claim 1, further comprising the steps of:

moving said samples relative to said dispensing station; and arranging said samples so that respective ones of said samples are fed to said dispensing station in the same order as corresponding groups of slides are moved through said dispensing station.

5. The analytical method of claim 1, further comprising the step of:

providing said partition plate with an identification mark identifying said partition plate as a partition plate.

6. The analytical method of claim 5, further comprising the step of:

making said partition plate white without opaque bars.

7. The analytical method of claim 5, further comprising the step of forming said identification mark as two bars.

8. The analytical method of claim 5, further comprising the steps of:

providing said partition plate with a sample identifying code;

providing respective identifying codes on containers containing said samples; and moving into said dispensing station a container carrying a sample-identifying code corresponding to said sample-identifying code on said partition plate.

9. The analytical method of claim 5, wherein said identification mark is a bar code, and further comprising the step of providing an identical bar code on a container of one of said samples to be dispensed on said second group of chemical analytical slides at said dispensing station; and moving said container having said bar code identical to said bar code on said partition plate so as to dispense said one of said samples onto said next adjacent group of slides at said dispensing station.

10. The analytical method of claim 9, further comprising a step of providing an order of a plurality of containers in said analyzer inconsistent with an order of said chemical analytical slides loaded in said analyzer.

11. An automatic dispensing apparatus for an analytical analyzer comprising:

means for storing a plurality of chemical analytical slides and a partition plate, said plurality of chemical analytical slides being arranged in groups and said partition plate dividing adjacent groups of chemical analytical slides, wherein said partition plate is optically discriminable;

means for storing a plurality of samples;

means for automatically moving said chemical analytical slides and said partition plate through a dispensing station to a chemical analyzer;

means for selectively dispensing said samples onto respective groups of said chemical analytical slides at said dispensing station;

means for detecting the presence of said partition plate dividing adjacent groups of chemical analytical slides; and means, responsive to an output signal from said detecting means representing a detection of said partition plate, for moving one of said samples into said dispensing station so that said one of said samples is immediately dispensed onto its respective group of chemical analytical slides.

12. An apparatus of claim 11, wherein said means for storing samples comprises a rotatable tray having disposed thereon a container for each of said samples.

13. An apparatus of claim 11, wherein said dispensing means comprises a pipette movable between said containers and said dispensing station.

14. An apparatus of claim 11, wherein said means for detecting comprises means for reading on said slides identification marks identifying sample characteristics to be analyzed, and for reading on said partition plate a sample-identifying code;

wherein said means for storing chemical analytical slides comprises a cartridge for vertically storing said slides and said partition plate;

wherein said means for storing samples comprises a rotatable tray having disposed thereon a plurality of containers for respective samples, each container having a sample-identifying code; and wherein said means for moving said samples comprises means for reading said code on said container and rotates said tray so that a sample in a container, having a sample-identifying code corresponding to said sample identifying code on said partition plate, is dispensed at said dispensing station.

15. The apparatus of claim 14, wherein an order of said containers positioned on said rotatable tray is inconsistent with an order of said chemical analytical slides stacked in said cartridge.

* * * * *